United States Patent
Cohen et al.

(10) Patent No.: US 10,410,404 B2
(45) Date of Patent: *Sep. 10, 2019

(54) SELECTING POINTS ON A ELECTROANATOMICAL MAP

(71) Applicant: BIOSENSE WEBSTER (ISRAEL) LTD., Yokneam (IL)

(72) Inventors: Assaf Cohen, Kiryat Bialik (IL); Fady Massarwi, Baka Al Gharbiyya (IL); Ido Ilan, Yoqneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,654

(22) Filed: Oct. 2, 2018

(65) Prior Publication Data

US 2019/0035141 A1   Jan. 31, 2019

Related U.S. Application Data

(63) Continuation of application No. 15/394,980, filed on Dec. 30, 2016, now Pat. No. 10,102,665.

(51) Int. Cl.
*G06T 15/10* (2011.01)
*A61B 5/044* (2006.01)
(Continued)

(52) U.S. Cl.
CPC ............. *G06T 15/10* (2013.01); *A61B 5/044* (2013.01); *G06F 3/048* (2013.01);
(Continued)

(58) Field of Classification Search
CPC .................................................. A61B 5/04012
See application file for complete search history.

(56) References Cited

U.S. PATENT DOCUMENTS

| 4,974,598 A | 12/1990 | John |
| 6,208,347 B1 | 3/2001 | Migdal et al. |

(Continued)

FOREIGN PATENT DOCUMENTS

WO    WO 2010/054320    5/2010

OTHER PUBLICATIONS

Sethian, James A., "A fast marching level set method for monotonically advancing fronts", Proc. Natl. Acad. Sci. USA, Feb. 1996, pp. 1591-1595, vol. 93.

(Continued)

*Primary Examiner* — Jitesh Patel
(74) *Attorney, Agent, or Firm* — Vincent J. Serrao

(57) ABSTRACT

Described embodiments include a system that includes a display and a processor. The processor is configured to position an indicator, in response to a positioning input from a user, over a particular point on a three-dimensional electroanatomical map that is displayed on the display, and over which are displayed a plurality of markers that mark respective data points. The processor is further configured to expand a contour, subsequently, along a surface of the map, while a selecting input from the user is ongoing, such that all points on the contour remain equidistant, at an increasing geodesic distance with respect to the surface, from the particular point, and to display, on the display, one or more properties of each of the data points that is marked by a respective one of the markers that is inside the contour. Other embodiments are also described.

16 Claims, 4 Drawing Sheets

(51) Int. Cl.
  *G06F 3/0481* (2013.01)
  *G06F 3/0484* (2013.01)
  *G06T 19/20* (2011.01)
  *G06F 3/048* (2013.01)
  *G06F 3/0488* (2013.01)

(52) U.S. Cl.
  CPC ...... *G06F 3/04812* (2013.01); *G06F 3/04815* (2013.01); *G06F 3/04845* (2013.01); *G06F 3/04883* (2013.01); *G06T 19/20* (2013.01); *G06F 2203/04806* (2013.01); *G06T 2200/24* (2013.01); *G06T 2210/41* (2013.01); *G06T 2219/016* (2013.01); *G06T 2219/2016* (2013.01)

(56) References Cited

U.S. PATENT DOCUMENTS

| | | | |
|---|---|---|---|
| 6,256,038 | B1 | 7/2001 | Krishnamurthy |
| 6,456,867 | B2 | 9/2002 | Reisfeld |
| 6,577,319 | B1 | 6/2003 | Kashiwagi et al. |
| 6,650,927 | B1 | 11/2003 | Keidar |
| 7,468,731 | B2 | 12/2008 | Eldridge et al. |
| 7,626,589 | B2 | 12/2009 | Berger |
| 7,689,021 | B2 | 3/2010 | Shekhar et al. |
| 7,796,790 | B2 | 9/2010 | McNutt et al. |
| 7,805,181 | B2 | 9/2010 | Breeuwer |
| 8,155,400 | B2 | 4/2012 | Bronstein et al. |
| 8,174,535 | B2 | 5/2012 | Berger et al. |
| 8,270,693 | B2 | 9/2012 | Zou et al. |
| 8,788,029 | B2 | 7/2014 | Madry et al. |
| 8,907,944 | B2 | 12/2014 | Lin et al. |
| 9,129,417 | B2 | 9/2015 | Zheng et al. |
| 2006/0241445 | A1 | 10/2006 | Altmann et al. |
| 2007/0232949 | A1 | 10/2007 | Saksena |
| 2008/0188962 | A1* | 8/2008 | Suryanarayanan .. G06K 9/4638 700/89 |
| 2009/0214097 | A1 | 8/2009 | Mohamed et al. |
| 2010/0027861 | A1 | 2/2010 | Shekhar et al. |
| 2010/0215245 | A1* | 8/2010 | Olivan Bescos ..... G06T 3/0006 382/133 |
| 2011/0122136 | A1 | 5/2011 | Jo |
| 2011/0306896 | A1 | 12/2011 | Altmann |
| 2012/0101398 | A1* | 4/2012 | Ramanathan ...... A61B 5/04012 600/523 |
| 2013/0050207 | A1 | 2/2013 | Lin et al. |
| 2013/0222368 | A1 | 8/2013 | Takama et al. |
| 2014/0247284 | A1 | 9/2014 | Gooding et al. |
| 2014/0330111 | A1 | 11/2014 | Lichtenstein et al. |
| 2015/0367578 | A1 | 12/2015 | Arisoy et al. |

OTHER PUBLICATIONS

European Search Report dated May 3, 2018 from corresponding European Patent Application No. 17211197.3.

Paragios, Nikos, "A Variational Approach for the Segmentation of the Left Ventricle in Cardiac Image Analysis", International Journal of Computer Vision, Dec. 1, 2002, pp. 345-362, vol. 50, No. 3.

Wilson, K. et al., "Mapping of Cardiac Electrophysiology Onto a Dynamic Patient-Specific Heart Model", IEEE Transactions on Medical Imaging, Dec. 1, 2009, pp. 1870-1880, vol. 28, No. 12.

* cited by examiner

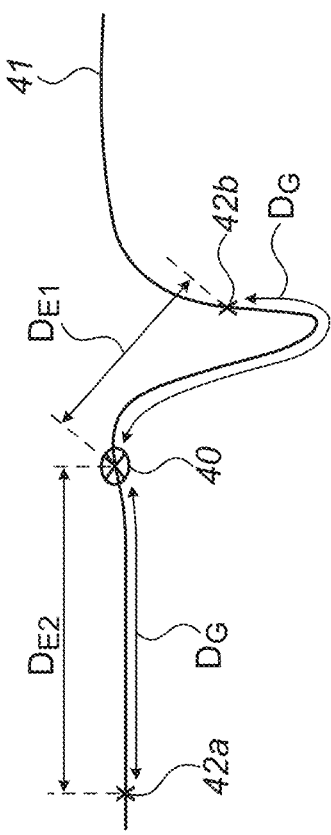
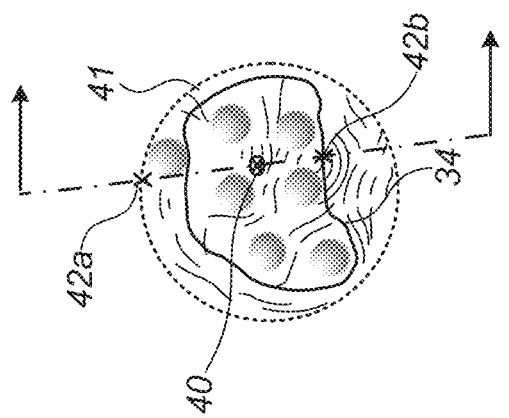
FIG. 3

US 10,410,404 B2

SELECTING POINTS ON A ELECTROANATOMICAL MAP

CROSS REFERENCE TO RELATED APPLICATION

This application is a Continuation of U.S. patent application Ser. No. 15/394,980, filed Dec. 30, 2016, the entire content of which is incorporated herein by reference.

FIELD OF THE INVENTION

The present invention relates to methods and interfaces for interacting with computer-rendered models, such as computer-rendered models of anatomical surfaces.

BACKGROUND

Three-dimensional surfaces are often represented in computer memory by a contiguous collection of tiles, such as triangular tiles. Such a representation may be referred to as a "tesselation" or a "mesh."

A "geodesic distance," with respect to a given surface, between two points that lie on the surface, is the length of the shortest path, along the surface, that connects the two points. For points lying on a curved surface, this distance is often different from the Euclidean distance between the points. For example, the geodesic distance between two hilltops is the length of the shortest path that runs, along the surface of the Earth, between the two hilltops. This distance is larger than the Euclidean distance between the hilltops, which is the length of a straight path, through the air, passing between the hilltops.

SUMMARY OF THE INVENTION

There is provided, in accordance with some embodiments of the present invention, a system that includes a display and a processor. The processor is configured to position an indicator, in response to a positioning input from a user, over a particular point on a three-dimensional electroanatomical map that is displayed on the display, and over which are displayed a plurality of markers that mark respective data points. The processor is further configured to expand a contour, subsequently, along a surface of the map, while a selecting input from the user is ongoing, such that all points on the contour remain equidistant, at an increasing geodesic distance with respect to the surface, from the particular point, and to display, on the display, one or more properties of each of the data points that is marked by a respective one of the markers that is inside the contour.

In some embodiments, the indicator includes a cursor.

In some embodiments, the selecting input includes a click of a button of a mouse.

In some embodiments, the processor is further configured to display the contour on the display while expanding the contour.

In some embodiments, the electroanatomical map includes an electroanatomical map of a surface of a heart.

In some embodiments, the one or more properties include one or more electrical properties.

In some embodiments, the processor is further configured to set a speed of expansion of the contour, in response to a speed-indicating input from the user.

In some embodiments, the processor is configured to expand the contour with a varying speed of expansion.

In some embodiments, the processor is configured to vary the speed of expansion as a function of a number of the markers that are within a given area that lies ahead of the contour.

In some embodiments, the processor is configured to vary the speed of expansion as a function of a density of the markers that are within a given area that lies ahead of the contour.

There is further provided, in accordance with some embodiments of the present invention, a method that includes, using a processor, in response to a positioning input from a user, positioning an indicator over a particular point on a displayed three-dimensional electroanatomical map over which are displayed a plurality of markers that mark respective data points. The method further includes, subsequently, while a selecting input from the user is ongoing, expanding a contour along a surface of the map, such that all points on the contour remain equidistant, at an increasing geodesic distance with respect to the surface, from the particular point, and displaying one or more properties of each of the data points that is marked by a respective one of the markers that is inside the contour.

The present invention will be more fully understood from the following detailed description of embodiments thereof, taken together with the drawings, in which:

BRIEF DESCRIPTION OF THE DRAWINGS

FIG. 3 is a schematic cross-section through a surface of an electroanatomical map on which a contour is located, in accordance with some embodiments of the present invention.

DETAILED DESCRIPTION OF EMBODIMENTS

Overview

Figure 1:
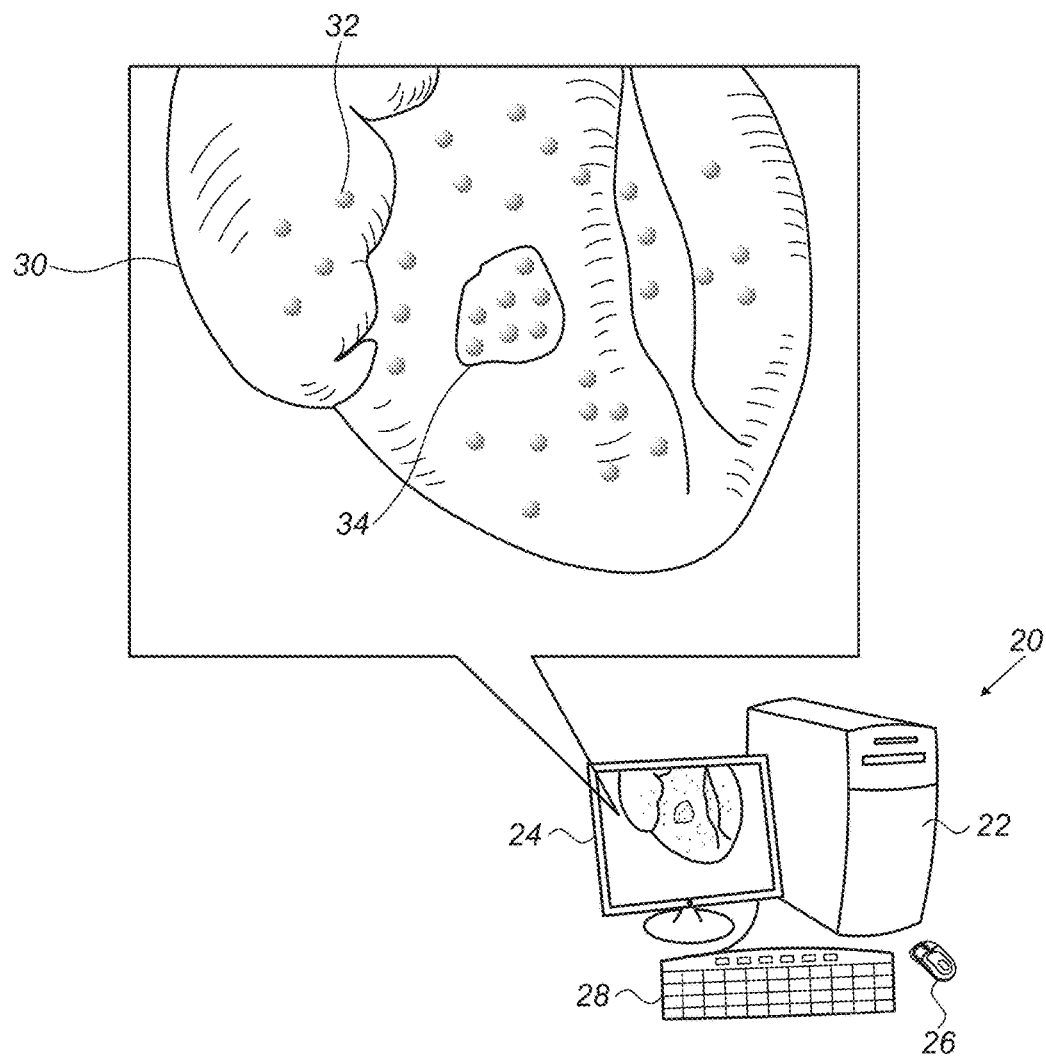
FIG. 1 is a schematic illustration of a system for selecting data points in a three-dimensional electroanatomical map, in accordance with some embodiments of the present invention.

In some embodiments, an electroanatomical map of a subject's heart is constructed. As implied by the word "electroanatomical," such a map combines anatomical information relating to the structure of the heart with information relating to the electrical activity of the heart. For example, the map may include a three-dimensional mesh, representing a surface of the heart, that is colored (or otherwise annotated) in accordance with local activation times (LATs), electrical potentials, and/or other properties that were measured at various locations on the surface. Such a mesh is typically constructed from a large number of data points, each of which corresponds to a particular location on the surface of heart at which the property of interest was measured. The mesh may be rendered on screen, with a plurality of markers indicating the respective locations of the data points.

In some cases, a user may wish to investigate, discard, edit, or otherwise process a cluster of data points located in a particular region of interest. To do this, the user must first select the relevant data points, by selecting the corresponding markers on the screen. However, performing such a selection may be tedious, particularly if the region of interest contains a large number of data points. For example, traditional "point-and-click" techniques require that the user separately click on each of the markers that corresponds to a data point of interest.

Embodiments of the present invention therefore provide improved techniques for selecting data points belonging to an electroanatomical map. In some embodiments, the user performs an extended mouse click, i.e., the user holds a mouse button in a clicked position, over a particular point of interest on the map. As the click is held, a contour expands outward from the particular point, such that all points on the contour remain equidistant, at an increasing geodesic distance, from the particular point. As the contour expands, the contour encapsulates any markers that it crosses, thus selecting the corresponding data points. When the user releases the mouse button, the contour stops expanding, and properties of all of the selected data points are displayed. In this manner, a large number of data points may be selected relatively quickly.

Moreover, by virtue of all points on the contour being geodesically equidistant from the point of interest, the selection of data points as described above is precise, i.e., the selection generally achieves a result that is similar to that which would have been achieved had the user manually clicked on all of the markers in the user's region of interest. This is because the geodesic distance between two points on the surface of the heart is generally correlated to the amount of time required for bioelectric signals to propagate between the two points, since such signals travel along the surface of the heart. Since, typically, a user (such as an electrophysiologist) would like to select a groups of data points that are within a particular propagation time of a point of interest, selecting data points according to their geodesic distance from the point of interest achieves the user's objective.

In other embodiments, the user is provided with a virtual brush, which the user may move across the display, e.g., using a mouse. As the brush moves over markers that are displayed on the map, the corresponding data points are selected.

It is noted that embodiments described herein may be applied to the selection of points of any type, belonging to any sort of three dimensional model that is rendered on screen. Alternatively, embodiments described herein may be used to identify a region of the model that is within a particular geodesic distance of a point of interest, without necessarily performing any point selection.

(It is noted that a contour is said to be at a particular geodesic distance from a point of interest on a map of an anatomical surface, if the contour is superimposed over the set of points on the map that correspond, respectively, to locations on the anatomical surface that are at the particular geodesic distance from the location on the anatomical surface to which the point of interest corresponds.)

System Description

Reference is initially made to FIG. 1, which is a schematic illustration of a system 20 for selecting data points in a three-dimensional electroanatomical map, in accordance with some embodiments of the present invention. System 20 comprises a processor 22 and a display 24, and may further comprise one or more input devices, such as a mouse 26 and/or a keyboard 28.

As shown in FIG. 1, processor 22 may display, on display 24, a three-dimensional electroanatomical map 30, such as a map of a surface of a subject's heart. As described above, electroanatomical map 30 may be constructed from a plurality of data points, each of which may be marked by a respective marker 32 displayed over the electroanatomical map. As described in detail below, a user may use display 24, mouse 26, keyboard 28, and/or any other input device to interact with the electroanatomical map. For example, as described below, the user may use the mouse to expand a contour 34 along the surface of the electroanatomical map, thus selecting a plurality of data points.

In general, processor 22 may be embodied as a single processor, or as a cooperatively networked or clustered set of processors. Processor 22 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
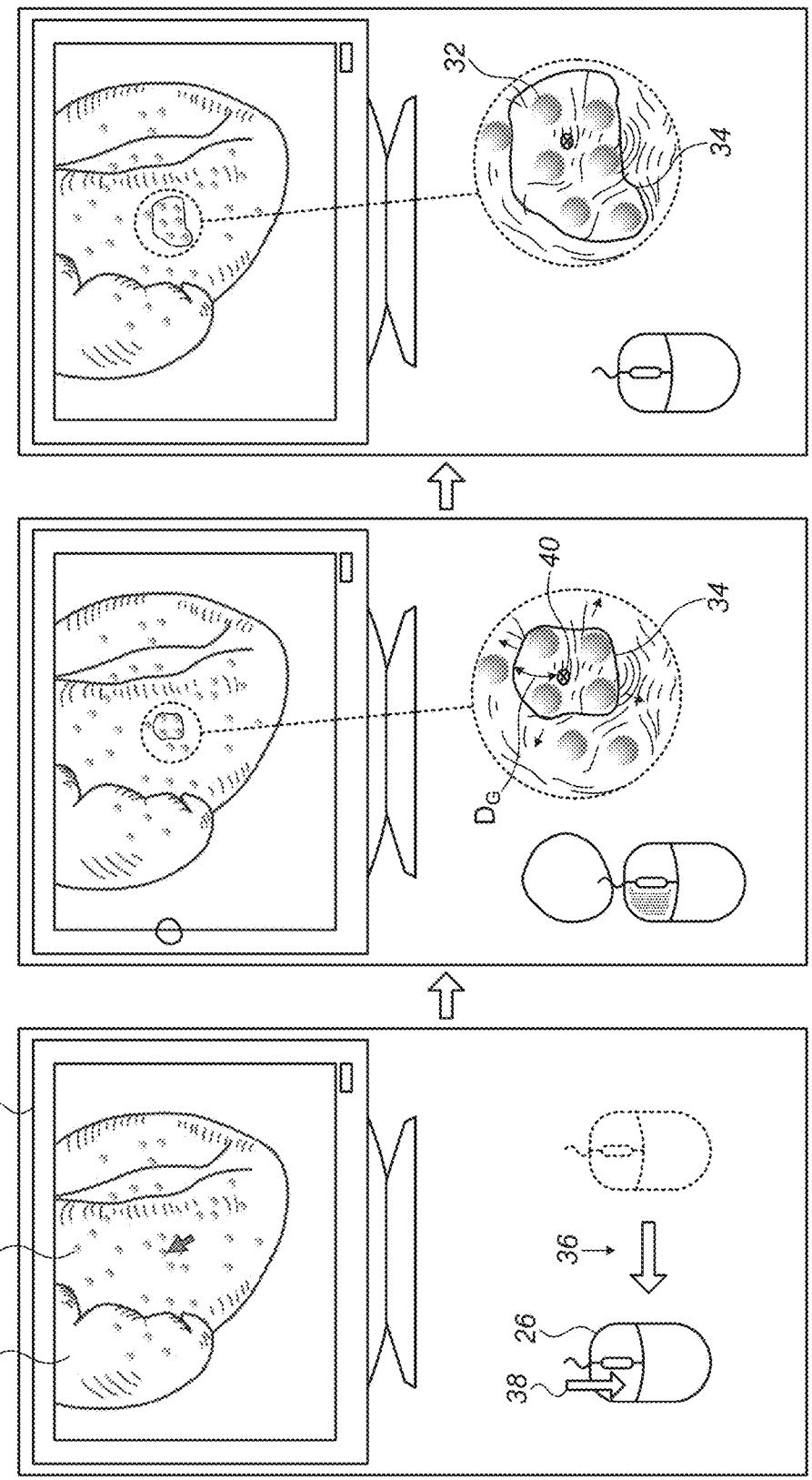
FIG. 2 is a schematic illustration of a method, performed by a processor, for selecting data points in a three-dimensional electroanatomical map, in accordance with some embodiments of the present invention.

Reference is now made to FIG. 2, which is a schematic illustration of a method, performed by processor 22, for selecting data points in a three-dimensional electroanatomical map, in accordance with some embodiments of the present invention.

First, as shown in the left portion of FIG. 2, processor 22 receives a positioning input 36 from the user. For example, as illustrated in FIG. 2, positioning input 36 may include a movement of mouse 26. In response to positioning input 36, the processor positions a cursor 39 over a particular point on the displayed three-dimensional electroanatomical map, per the positioning input. Alternatively, the processor may receive any other suitable type of positioning input (e.g., a pressing of arrow keys on keyboard 28, or suitable gestures performed on a touch-screen of display 24), and, in response thereto, position cursor 39, or any other suitable indicator, over the particular point indicated by the positioning input.

Subsequently, the user begins a selecting input 38, e.g., by clicking a button of mouse 26, or by pressing a key on keyboard 28. Then, as shown in the middle portion of FIG. 2, while selecting input 38 is ongoing (e.g., while the mouse-button click is held), the processor expands contour 34 along a surface of the electroanatomical map, such that all points on the contour remain equidistant, at an increasing geodesic distance $D_G$ with respect to the surface, from the particular point 40 at which the cursor was positioned. Typically, the processor displays the contour while expanding the contour. In some embodiments, while the contour is expanding, the user may rotate the electroanatomical map, zoom in to or out from the electroanatomical map, or otherwise adjust his view of the electroanatomical map.

As the selecting input is held, the processor repeatedly re-computes the contour at an increased geodesic distance from the point of interest. Geodesic distances may be computed using any suitable techniques known in the art, such as Dijksta's algorithm, or the fast marching method, described in Sethian, James A., "A fast marching level set method for monotonically advancing fronts," Proceedings of the National Academy of Sciences 93.4 (1996): 1591-1595, which is incorporated herein by reference.

In some embodiments, the speed at which contour 34 is expanded remains fixed during the expansion of the contour. This speed may be set by the processor in response to a speed-indicating input from the user. For example, the user may enter a desired contour-expansion speed using keyboard 28. In other embodiments, the speed of expansion varies during the expansion of the contour. For example, the speed of expansion may increase as the contour grows larger, and/or may vary as a function of the number and/or density of markers within a given area that lies ahead of the contour. Thus, for example, the contour may expand more quickly into areas of the map that contain relatively few markers, and less quickly into areas of the map that contain more markers. In such embodiments, an initial speed of expansion, a rate of acceleration of expansion, and/or any other relevant parameters of the expansion may be set by the processor in response to input from the user.

Finally, as shown in the right portion of FIG. 2, selecting input 38 ends. In response to the end of the selecting input, the processor stops the expansion of contour 34.

Following the end of the expansion of the contour, the processor displays one or more properties of each of the data points that is marked by a respective one of markers 32 that is inside the contour. Alternatively or additionally, the processor may display these properties as the contour is expanding. For example, each time the contour passes, and hence encapsulates, another one of the markers, the processor may display the properties of the data point that is marked by the newly-encapsulated marker.

Reference is now made to FIG. 3, which is a schematic cross-section through a surface 41 on which contour 34 is located, in accordance with some embodiments of the present invention.

The cross-section of FIG. 3 "cuts through" contour 34 at two points: a first contour-point 42a, and a second contour-point 42b. As noted above, all of the points on contour 34 are at an equal geodesic distance from point 40. Thus, first contour-point 42a and second contour-point 42b are shown lying at an equal geodesic distance $D_G$ from point 40. To avoid any confusion, it is emphasized that a geodesic distance between two points is measured along the surface on which the points lie, and may therefore be different from the Euclidean distance between the points. For example, in FIG. 3, the Euclidean distance $D_{E1}$ between point 40 and second contour-point 42b is less than the Euclidean distance $D_{E2}$ between point 40 and first contour-point 42a, despite these points being at an equal geodesic distance from point 40.

In general, as noted above in the Overview, the geodesic distance between two points on the surface of the heart is correlated to the amount of time required for bioelectric signals to propagate between the two points, since such signals travel along the surface of the heart. Hence, geodesic distance corresponds to the manner in which a typical user (such as an electrophysiologist) thinks of "distance" between points on the surface of the heart. The selection of data points using contour 34 thus generally achieves a result that is similar to that which would have been achieved had the user manually clicked on all of the markers in the user's region of interest.

As noted above, each of the data points in electroanatomical map 30 may include various properties, such as electrical properties, of the surface of heart. Following the selection of the data points, the processor displays, on display 24, one or more of these properties, for each of the selected data points. For example, the processor may display a respective LAT and/or electrical potential of each of the selected data points. Alternatively or additionally, such properties may be displayed in "real-time," as the contour is expanding, for each data point encapsulated by the contour.

Figure 4:
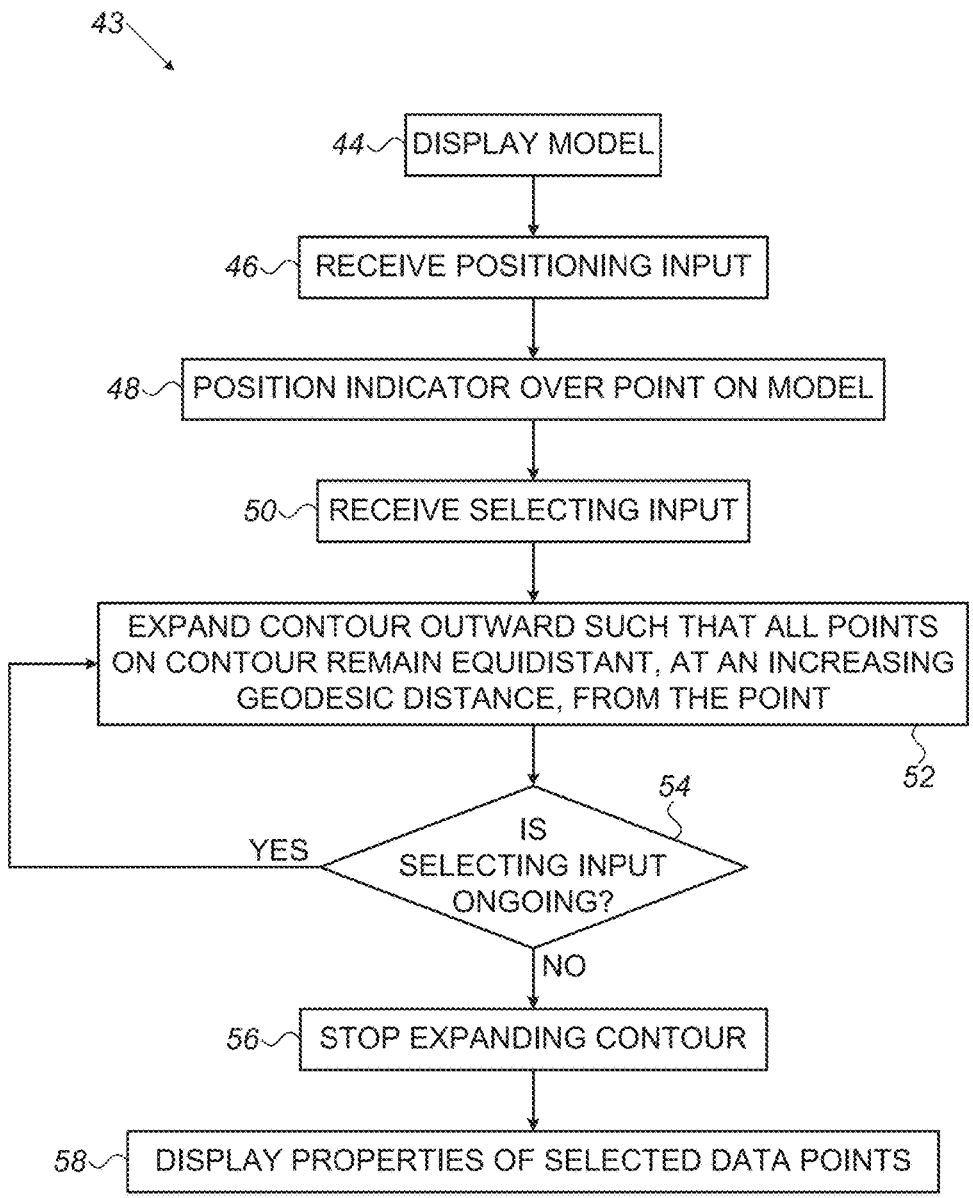
FIG. 4 is a flow diagram for a method for selecting data points, which is executed by a processor in accordance with some embodiments of the present invention.

Reference is now made to FIG. 4, which is a flow diagram for a method 43 for selecting data points, which is executed by processor 22 in accordance with some embodiments of the present invention. In general, most of the steps of method 43 were already described above, but are nonetheless described again, in brief, below, with reference to FIG. 4.

First, at a model-displaying step 44, the processor displays a three-dimensional model, such as the electroanatomical map described above. The processor then, at a positioning-input-receiving step 46, receives a positioning input from a user. In response thereto, the processor, at a positioning step 48, positions an indicator over a particular point on the model, as indicated by the positioning input. Next, at a selecting-input-receiving step 50, the processor receives a selecting input from the user. In response thereto, at a contour-expanding step 52, the processor expands a contour outward, along the surface of the model, from the particular point, such that all points on the contour remain equidistant, at an increasing geodesic distance, from the point. While expanding the contour, the processor continually checks, at a checking step 54, whether the selecting input is ongoing. If yes, the processor continues expanding the contour. Otherwise, at a stopping step 56, the processor stops expanding the contour. Finally, at a property-displaying step 58, the processor displays the properties of the selected data points. (As noted above, property-displaying step 58 may be executed earlier, while the contour is expanding.)

In other embodiments, the user is provided with a virtual brush, which the user then passes over the model, e.g., by dragging the brush with mouse 26. As the brush passes over the model, data points marked by the markers over which the brush passes are selected. In some embodiments, the processor colors, shades, or otherwise marks portions of the model over which the brush has passed, and/or enlarges or otherwise changes the form of markers 32 over which the brush has passed, to indicate to the user the data points that have been selected. While passing the brush over the model, the user may rotate the model, zoom in to or out from the model, or otherwise adjust his view of the model.

The processor typically positions the brush above, or in front of, the model, relative to the perspective of the user who is viewing the screen of display 24. As the user moves the brush across the model, the processor projects a virtual three-dimensional object from the brush "into" the screen, such that the object intersects the surface of the model. The processor identifies the area of the surface over which the intersection occurs, and then selects any data points whose markers are within this area. For example, as the user moves a circular brush across the screen, the processor may compute the area over which a virtual cylinder projected from the brush intersects the surface of the model, and may then select any data points whose markers are within this area.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a display; and
   a processor operatively connected to the display, configured to:
   position an indicator, in response to a positioning input from a user, over a particular point on a three-dimensional electroanatomical map that is displayed on the display, and over which are displayed a plurality of markers that mark respective data points;
   increasingly expand a contour over time along a surface of the map, while a selecting input from the user is ongoing, such that all points on the contour remain at an equidistant geodesic distance with respect to the surface, from the particular point at the same time; and
   display, on the display, one or more properties of each of the data points that is marked by a respective one of the markers that is inside the contour.

2. The system according to claim 1, wherein the indicator includes a cursor.

3. The system according to claim 1, wherein the selecting input includes a click of a button of a mouse.

4. The system according to claim 1, wherein the processor is further configured to display the contour on the display while expanding the contour.

5. The system according to claim 1, wherein the electroanatomical map includes an electroanatomical map of a surface of a heart.

6. The system according to claim 5, wherein the one or more properties include one or more electrical properties.

7. The system according to claim 1, wherein the processor is further configured to set a speed of expansion of the contour, in response to a speed-indicating input from the user.

8. The system according to claim 1, wherein the processor is configured to expand the contour with a varying speed of expansion.

9. A method, comprising:
   using a processor, in response to a positioning input from a user, positioning an indicator over a particular point on a displayed three-dimensional electroanatomical map over which are displayed a plurality of markers that mark respective data points;
   subsequently, while a selecting input from the user is ongoing, increasingly expanding a contour over time along a surface of the map, such that all points on the contour remain at an equidistant geodesic distance with respect to the surface, from the particular point at the same time; and
   displaying one or more properties of each of the data points that is marked by a respective one of the markers that is inside the contour.

10. The method according to claim 9, wherein the indicator includes a cursor.

11. The method according to claim 9, wherein the selecting input includes a click of a button of a mouse.

12. The method according to claim 9, further comprising displaying the contour while expanding the contour.

13. The method according to claim 9, wherein the electroanatomical map includes an electroanatomical map of a surface of a heart.

14. The method according to claim 13, wherein the one or more properties include one or more electrical properties.

15. The method according to claim 9, further comprising setting a speed of expansion of the contour, in response to a speed-indicating input from the user.

16. The method according to claim 9, wherein expanding the contour comprises expanding the contour with a varying speed of expansion.

* * * * *